US012575821B2

(12) United States Patent
Halevy

(10) Patent No.: US 12,575,821 B2
(45) Date of Patent: Mar. 17, 2026

(54) DEVICE FOR THE STITCHING OF LAPAROSCOPIC INCISIONS AND METHODS THEREOF

(71) Applicant: Ariel Halevy, Rishon Lezion (IL)

(72) Inventor: Ariel Halevy, Rishon Lezion (IL)

( * ) Notice: Subject to any disclaimer, the term of this patent is extended or adjusted under 35 U.S.C. 154(b) by 608 days.

(21) Appl. No.: 17/791,227

(22) PCT Filed: Feb. 7, 2021

(86) PCT No.: PCT/IL2021/050145
§ 371 (c)(1),
(2) Date: Jul. 7, 2022

(87) PCT Pub. No.: WO2021/152604
PCT Pub. Date: Aug. 5, 2021

(65) Prior Publication Data
US 2023/0085002 A1 Mar. 16, 2023

Related U.S. Application Data

(60) Provisional application No. 62/957,807, filed on Jan. 7, 2020.

(51) Int. Cl.
A61B 17/04 (2006.01)
A61B 17/00 (2006.01)

(52) U.S. Cl.
CPC ...... A61B 17/0469 (2013.01); A61B 17/0057 (2013.01); A61B 2017/00637 (2013.01); A61B 2017/047 (2013.01)

(58) Field of Classification Search
CPC ............ A61B 17/0469; A61B 17/0057; A61B 2017/00637; A61B 2017/047
See application file for complete search history.

(56) References Cited

U.S. PATENT DOCUMENTS

| | | | | |
|---|---|---|---|---|
| 5,320,632 A | * | 6/1994 | Heidmueller ...... A61B 17/0469 | 112/169 |
| 5,374,275 A | | 12/1994 | Bradley et al. | |
| 2007/0213757 A1 | | 9/2007 | Boraiah | |

FOREIGN PATENT DOCUMENTS

| | | |
|---|---|---|
| EP | 0542126 A2 | 5/1993 |
| GB | 2440792 A | 2/2008 |

OTHER PUBLICATIONS

PCT International Search Report for International Application No. PCT/IL2021/050145, mailed Mar. 25, 2021, 3pp.
(Continued)

*Primary Examiner* — Erin McGrath
(74) *Attorney, Agent, or Firm* — The Roy Gross Law Firm, LLC; Roy D. Gross

(57) ABSTRACT

A device (300) for the suturing and closing of laparoscopic incisions, comprising: a. a central stem b. a plurality of ribs (34b) hingedly connected to said upper rib member by a locking joint (54), said lower rib member comprising a suture needle holder (36) at free end; c. a cap (33), d. a plurality of rigid stretchers (35), interconnected by a hinge to the distal end of said outer shaft (31a) and said upper rib member (34a); the outer shaft configured to slide along the inner shaft and urge said rigid stretchers to extend from a closed configuration of rib, stretcher and shaft in substantially parallel contact, to an open configuration defined by an angle subtended by said inner shaft (32) and said rigid stretchers (35).

8 Claims, 9 Drawing Sheets

(56) References Cited

OTHER PUBLICATIONS

PCT Written Opinion for International Application No. PCT/IL2021/050145, mailed Mar. 25, 2021, 7pp.

Jiang et al. (2014) "Experimental study of needle-tissue interaction forces: effect of needle geometries, insertion methods and tissue characteristics." (2014). Department of Radiation Oncology Faculty Papers. Paper 48. https://jdc.jefferson.edu/radoncfp/48.

* cited by examiner

DEVICE FOR THE STITCHING OF LAPAROSCOPIC INCISIONS AND METHODS THEREOF

This application is a National Phase of PCT Patent Application No. PCT/IL2021/050145 having International filing date of Feb. 7, 2021, which claims the benefit of priority of U.S. Provisional Patent Application No. 62/957,807, filed Jan. 7, 2020, the contents of which are all incorporated herein by reference in their entirety.

FIELD OF THE INVENTION

The present invention pertains to surgical devices, more particularly to devices for stitching laparoscopic incisions and for methods thereof.

BACKGROUND OF THE INVENTION

In 2017, the overall laparoscopy and endoscopy devices market was worth $18.39 billion and is growing with a CAGR (compound annual growth rate) of 4.80% in the forecast period, 2018-2025. Increasing number of surgical procedures performed using minimally invasive approaches (laparoscopy/endoscopy) is driving the growth of laparoscopy and endoscopy devices. Nearly 15 million laparoscopic procedures are performed every year, globally and the U.S. alone contributes to 32% of the number, i.e. around 4,800,000 procedures. Since the advent of laparoscopy in the 1990s, the technique is used to perform 1.2 million cholecystectomies.

In spite of the extensive use of this technique, a number of problems still exist. Closure of the trocar site may be difficult, specifically in the treatment of large or obese patients. Incomplete or faulty closure, such as that due to technical difficulties, can result in a hernia, specifically Post-Operative Ventral Hernia (POVH) or Incisional Hernia. Many devices have been proposed and produced for the closing of small laparoscopic opening, yet none are currently in clinical use. There exists hence a long felt need for a device for the closure of trocar sites in patents.

SUMMARY OF THE INVENTION

It is an object of the present invention to present a device 300 for the stitching and closing of laparoscopic incisions, comprising: a central stem having an outer hollow shaft 31 with a distal end 31a and a proximal end 31b; and an inner shaft 32 with a distal end 32a and a proximal end 32b the inner shaft slidably accommodated within the outer hollow shaft 31; a plurality of ribs 34 each comprising an upper rib member 34a and a lower rib member 34b hingedly connected to the upper rib member by a locking joint (FIG. 5 54), the lower rib member comprising a suture needle holder 36 at free end; a cap 33, mounted upon distal end of the inner shaft, the cap comprising a hinge connected to the upper rib member 34a; a plurality of rigid stretchers 35, interconnected by a hinge to the distal end of the outer shaft 31a and the upper rib member 34a; the outer shaft configured to slide along the inner shaft and urge said rigid stretchers to extend from a closed configuration of rib, stretcher and shaft in substantially parallel contact to an open configuration defined by an angle subtended by said inner shaft 32 and said rigid stretchers 35.

It is another object of the present invention to present the aforementioned device, as presented in any of the above, wherein the ribs 34 are juxtaposed in pairs.

It is another object of the present invention to present the device, as presented in any of the above, wherein the device in closed configuration has a smaller cross section than a trocar or cannula used in the laparoscopic procedure.

It is another object of the present invention to present the device, as presented in any of the above, wherein the device is further configured to secure a suture thread, the thread following a path defined by the juxtaposed ribs 34 and the cap 33, the ribs 34 and the cap 33 comprising suture thread holds selected from ridges, lips, flanges, rims, ribs, grooves, indents, pathways, hooks, brackets, shelfs, loops, hoops, eyes, eyelets and rings or similar.

It is another object of the present invention to present the device, as presented in any of the above, wherein the rib 50 and/or 34 additional comprises a middle member 53 connected to the upper member 51 and/or 34a and the lower member 34b and/or 52.

It is another object of the present invention to present the device, as presented in any of the above, wherein the rib 34 and/or 800 has a locking joint 54, connecting the middle member 53 and the lower member 34b and/or 52.

It is the object of the present invention to present a device 800 for the stitching of incisions, comprising: two ribs pivoted together in a middle portion thereof, each rib having a handle unit 81 at the proximal end and a suture needle holding unit 82 at the distal end, the two ribs are positioned to slide past each other; and a pivot 83 attaching the ribs; the ribs are configured to pivot scissors like from a closed position of both ribs inversely superimposed on the other 8b to an open configuration 8c.

It is another object of the present invention to present the device, as presented in any of the above, wherein the device is furthered configured to secure a suture thread 91, the thread 91 following a path defined by the ribs 92, the ribs 93 comprising holds selected from ridges, lips, flanges, rims, ribs, indents, pathways, hooks, grooves, brackets, shelfs, loops, hoops and rings.

It is the object of the present invention to present a method of stitching an opening in a patent, comprising steps of obtaining the suturing device of claim 1 and attaching sutures, comprising needles and attached thread; placing the device through a surgical opening into the surgical volume of the patient; opening the device and locating point of the suture needles around edges of the surgical opening; bridging the suture needle body at least partially through the physiological layers of the patient, suture needle shaft within the grasp of a medical operator; grasping the suture needle; detaching the suture from the device; closing the device; removing the device from the patient; passing the suture needles carrying the suture thread completely through the physiological layers of the patient; and stitching the opening.

It is another object of the present invention to present the method, as presented in any of the above, additionally comprising a step of placing a trocar through the opening.

It is another object of the present invention to present the method, as presented in any of the above, additionally comprising a step of removing the trocar through the opening.

It is the object of the present invention to present a method of stitching an opening in a patent, comprising steps of obtaining the aforementioned suturing device and attaching a suture, comprising needles and attached thread; placing the device through a surgical opening into the surgical volume of the patient; opening the device and locating point of the suture needles around edges of the surgical opening; bridging the suture needle body at least partially through the physiological layers of the patient, suture needle shaft within the grasp of a medical operator; grasping the suture needle; detaching the suture from the device; closing the device; removing the device from the patent; passing the suture needles carrying the suture thread completely through the physiological layers of the patent; and stitching the opening.

It is another object of the present invention to present the method, as presented in any of the above, additionally comprising a step of placing a trocar through the opening.

It is another object of the present invention to present the method, as presented in any of the above, additionally comprising a step of removing the trocar through the opening.

Other embodiments than described here are obvious to those skilled in the art and do not detract from the subject matter regarded as invention. A more complete understanding of the present invention, as well as further features and advantages of the present invention, will be obtained by reference to the following detailed description and drawings.

BRIEF DESCRIPTION OF THE FIGURES

The accompanying drawings, which are included to provide a further understanding of the invention and are incorporated in and constitute a part of this specification, illustrate embodiments of the invention and together with the description serve to explain the principles of the invention wherein.

DETAILED DESCRIPTION OF THE PREFERRED EMBODIMENT

The following description is provided, alongside all chapters of the present invention, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide compositions and methods.

Figure 1:
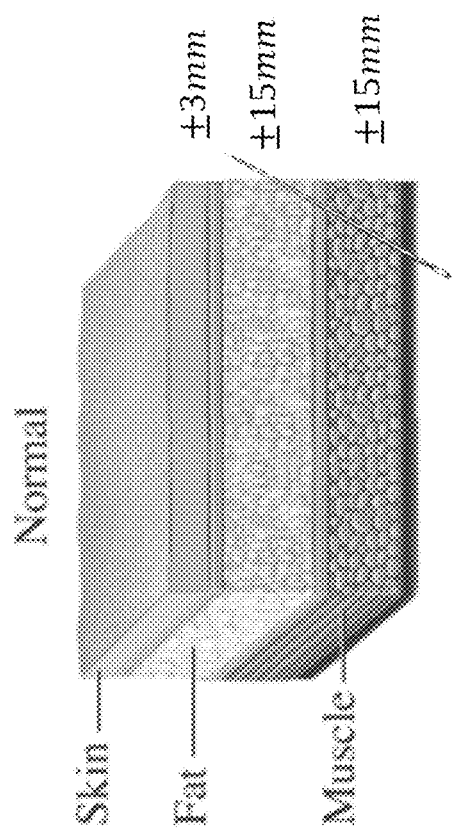
FIG. 1 schematically illustrates in an out of scale manner the physiological layers surrounding the laparoscopic surgical area according to one embodiment of the invention.

Laparoscopy is a minimally invasive surgical technique that typically involves making a small (about 0.5 to 1.5 cm) incision in the patent (such as in the abdominal wall, FIG. 1). The incision is made with and a trocar is placed into the volume, such as the abdomen. The trocar consist of the obturator (a bladed on non-bladed tip), a cannula (a hollow tube serving as a portal for the placement of surgical tools) and a seal (for the sealing the opening during operation).

In order to assess what would be necessary for the "Device of Choice" to close the trocar site. The following considerations are made: Operational limitations are operational vis the cannula and enable operation after/following removal of the trocar (closing opening through which the device enters). Operational guidelines are Easy for use, Quick to apply, Safe for the patient and Minimum risk of faulty closure.

General technological characteristics are as follows: The stitching instrument is inserted through the trocar and/or the cannula; into the peritoneum cavity so that the needle's direction is inside out (i.e. the tip of the needle faces outwards, towards the outer layer of the body, towards the skin). The needle must then enable passage of the suture through the muscle layer (about 5 mm), the fat layer (about 15 mm) and the skin (about 3 mm) (FIG. 1), such as with 0 or 1 needle. Specifically the needle passes through the peritoneum, muscle, subcutaneous and out sparing the skin. Prior to operation the needles are positioned a distance of about 0.8 to about 1 cm from the edges of the incision.

Figure 2:
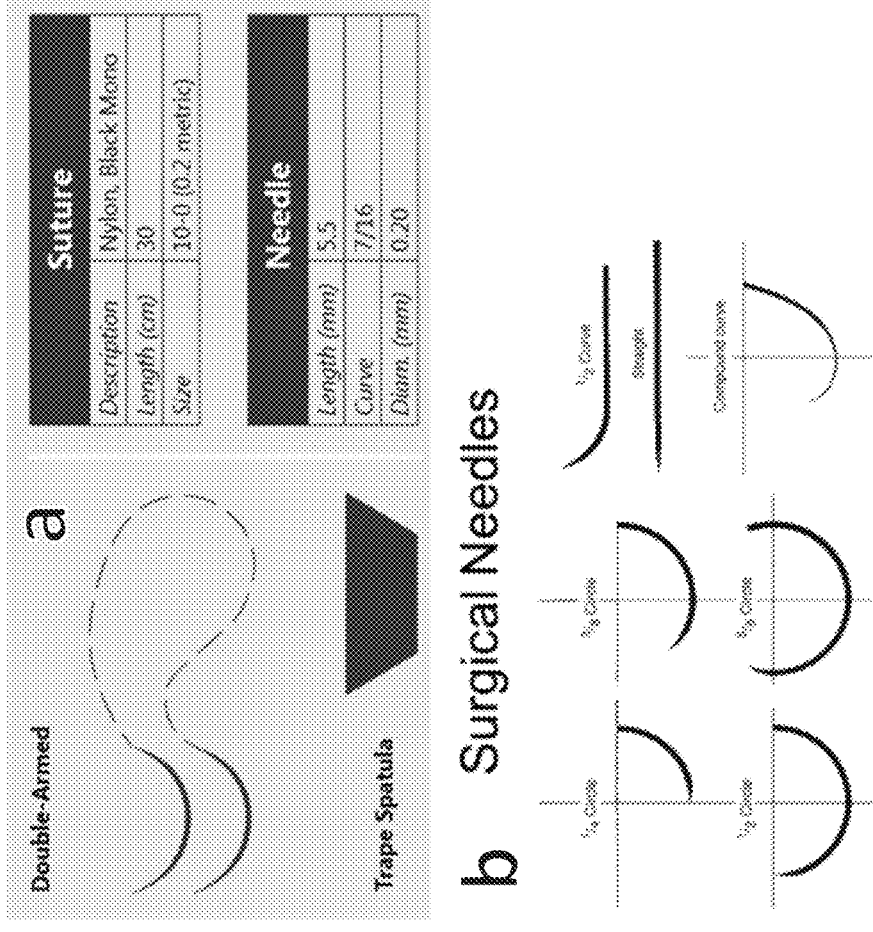
FIG. 2 schematically illustrates in an out of scale manner surgical sutures according to another embodiment of the invention.

FIG. 2*a* shows the typical of double-armed needle-suture construct used in surgery. FIG. 2*b* shows the variations in suture needle geometry.

Analysis has shown that a pressure of about 1 newton is optimal for suturing; see Jiang, Shan et al, 2014, Department of Radiation Oncology Faculty Papers, Paper 48 which is incorporated herein as a reference.

The essence of the technology of present invention is as defined below. It is the objection of the present invention to present a system/device comprising: at least one centre shaft for placing the device through an opening, such as a cannula and/or a trocar. In some embodiments, the handle has a grip on the proximal end. In some embodiments the handle comprises an inner shaft, and an outer shaft slider, so as the outer shaft slider is able to slide up and down the inner shaft in order manipulate position of the arms. At least a plurality of ribs is also provided, and attached to the distal end of the stem. The ribs are characterised as having at least two configurations: A closed configuration, forming a cross-section with a size suitable to pass through the opening (formed by a trocar and/or a cannula), so as to introduce and/or remove the device from the volume. The maximum cross-section of the closed configuration must be smaller than the diameter of the cannula (The minimum-bound circle of the closed configuration is smaller than the diameter of the cannula). An open configuration, designed to position the ribs juxtaposed to each-other, in pairs. The ribs are configured to hold at least one needle (in each rib), in a temporary and releasable manor, with the point facing in the outwards direction. In some embodiments, the thread suture is integrated, and or attached to the needle. In some embodiments, the ribs and cap are configured to hold the thread in place, so as to limit the movement of the thread during operation.

One embodiment of the present invention comprises one or more multiple interconnected ribs, called the also 'umbrella', and has a stem that comprises an inner shaft interconnected to the ribs by a hinge and an outer shaft slider interconnected to supports, further connected to the ribs. In this configuration the outer shaft slider is able to slide up and down the inner shaft and to control the position and opening of the ribs by the positioning the support.

Figure 3:
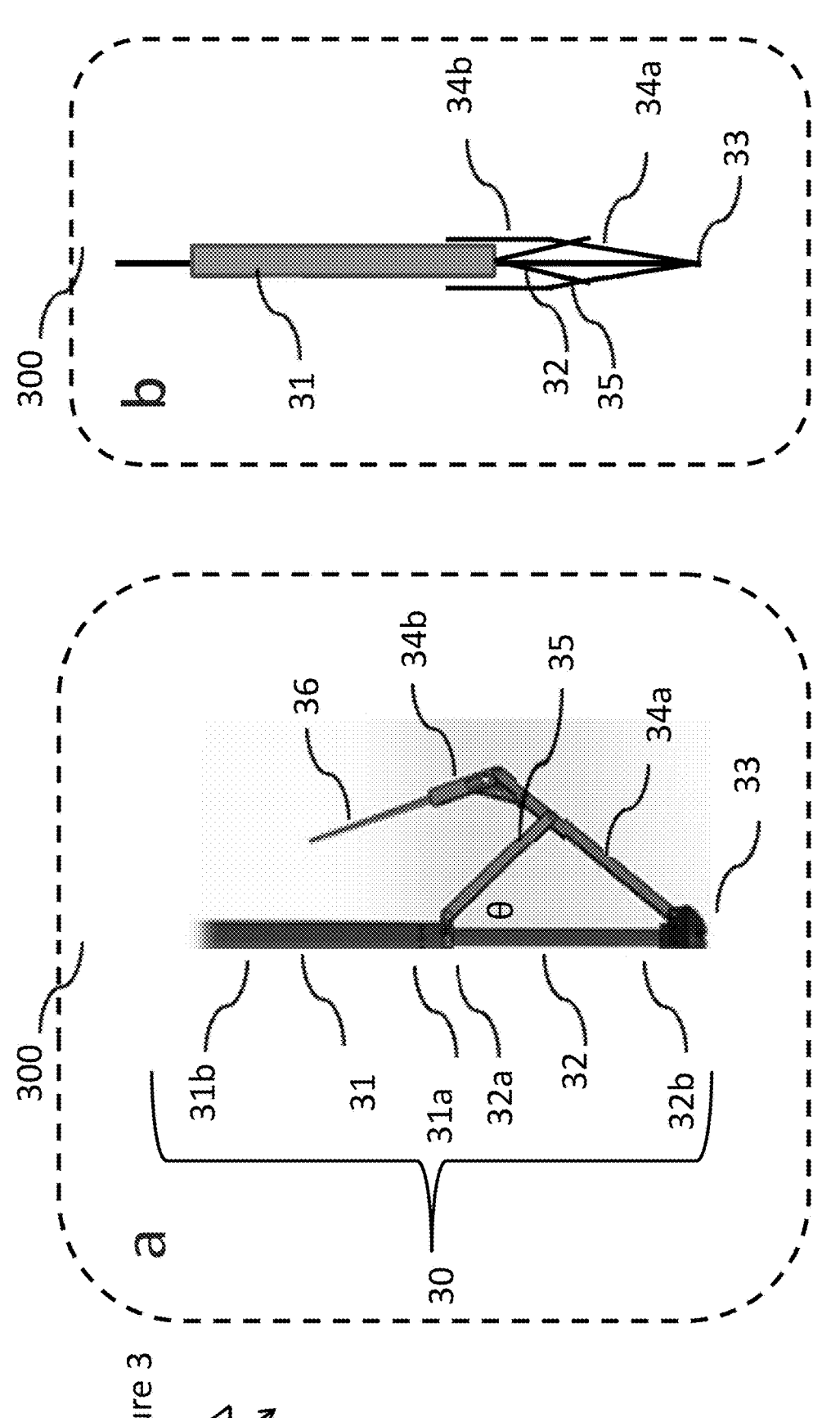
FIG. 3 schematically illustrates in an out of scale manner the (here e.g., 2 arms) umbrella configuration according to another embodiment of the invention.

The 'umbrella' configuration is presented in FIG. 3, showing a cross section of the device 300. FIG. 3a presents device in open configuration, with a main shaft 30, comprising an external shaft 31a connected to an internal shaft 31b, enabling the opening of the device. The ribs 34 are connected to the extender 31a through a cap 33. The cap 33 comprises a hinge between the internal shaft 31b and the ribs 34. In some embodiments, the rib is constructed from two members: an upper member 34a and a lower member 34b. In some embodiments, the ribs 34 are held in place by rigid stretchers 35, connected to the outer shaft 31b and the upper member 34a with hinges. The needles 36 are attached in a temporary manner to a lower member 34b, so as to position the needles 36 so as to suture the opening. FIG. 3b presents the device 300 in closed configuration.

Figure 4:
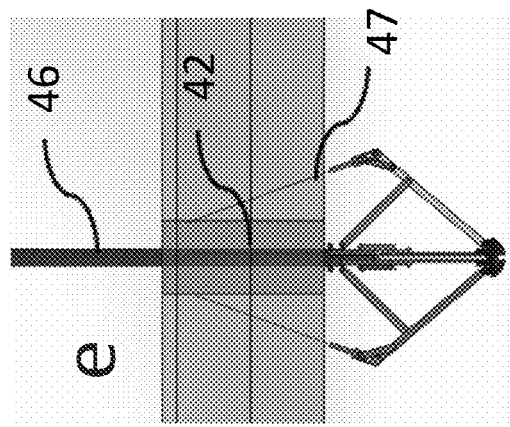
FIG. 4 schematically illustrates in an out of scale manner the operation of the (here e.g., 2 arms) "umbrella" configuration according to another embodiment of the invention.
Figure 4:
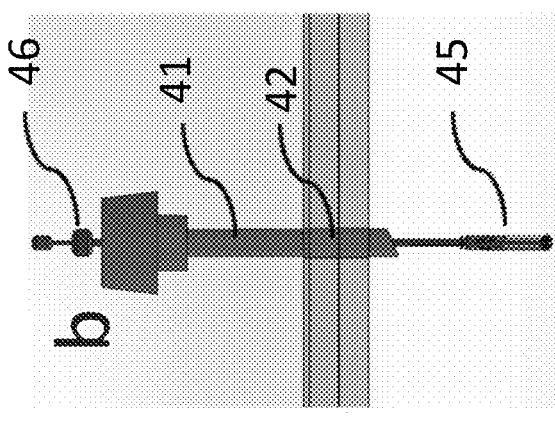
Figure 4:
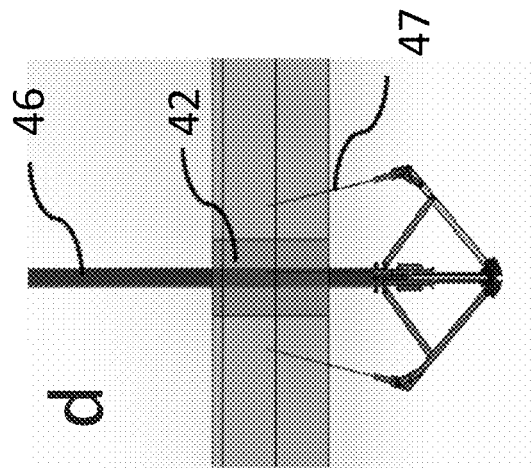
Figure 4:
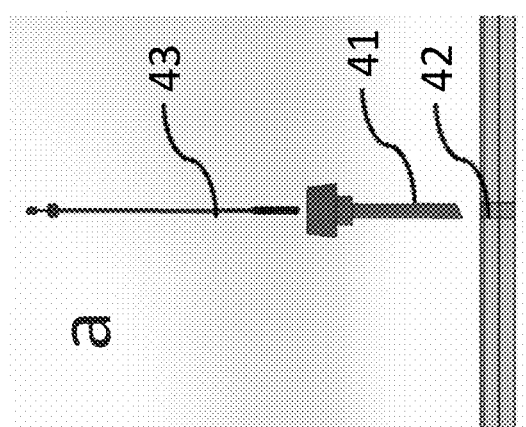
Figure 4:
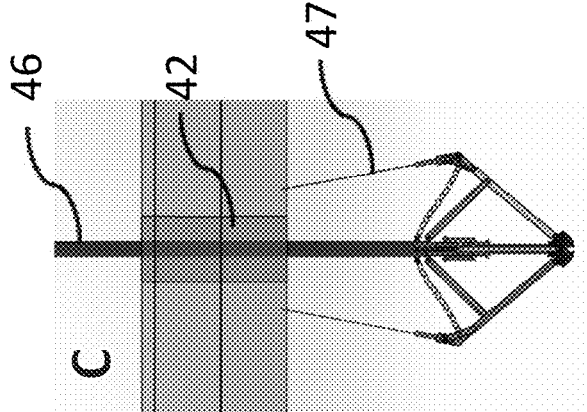
Figure 4:

Reference is made to FIG. 4, showing the introducing the device in the 'umbrella' configuration to the surgical volume. FIG. 4a shows the trocar 41 is being placed in or creating an opening 42, following which; the device 43 is placed through the cannula of the trocar 41. FIG. 4b shows the device placed in the surgical volume, via a trocar 41 placed in the opening 42, with the distil end 45 in the volume, in the closed conformation, and the proximal end outside 46 (towards the operator). FIG. 4c shows the device opened once placed in the volume, with the needles 47 facing outwards. FIGS. 4d and 4e demonstrate traversing of the physiological layers by the needle 47 by the raising of the handle 46 through the opening 42.

Figure 5:
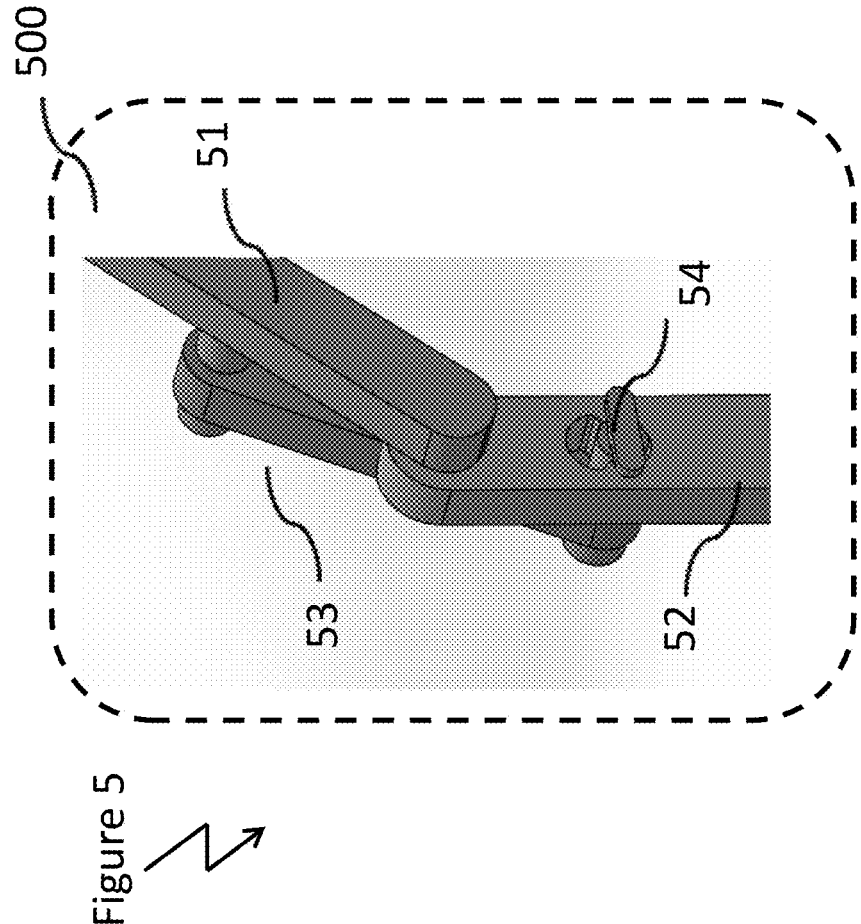
FIG. 5 schematically illustrates in an out of scale manner the locking mechanism of the (here e.g., 2 arms) umbrella configuration according to another embodiment of the invention.

Reference is made to FIG. 5, showing one embodiment of the arm construction 500, of the 'umbrella'. The upper member 51 is further connected to the lower member 52 with a hinge. Both the upper member 51 and lower member 52 are connected to an additional, middle member 53 with hinges. The hinge between the lower member 52 and the middle member 53 is connected with a locking mechanism 54 when in final position, for holding the rib position. In one embodiment the locking mechanizing comprises a slider with two positions, having Δ0.07 mm suppression. A suturing pressure of about 1 newton will not cause the release of the locking mechanism. The term about refers to a measure being greater than or lower than 20% of the defined value.

Figure 6:
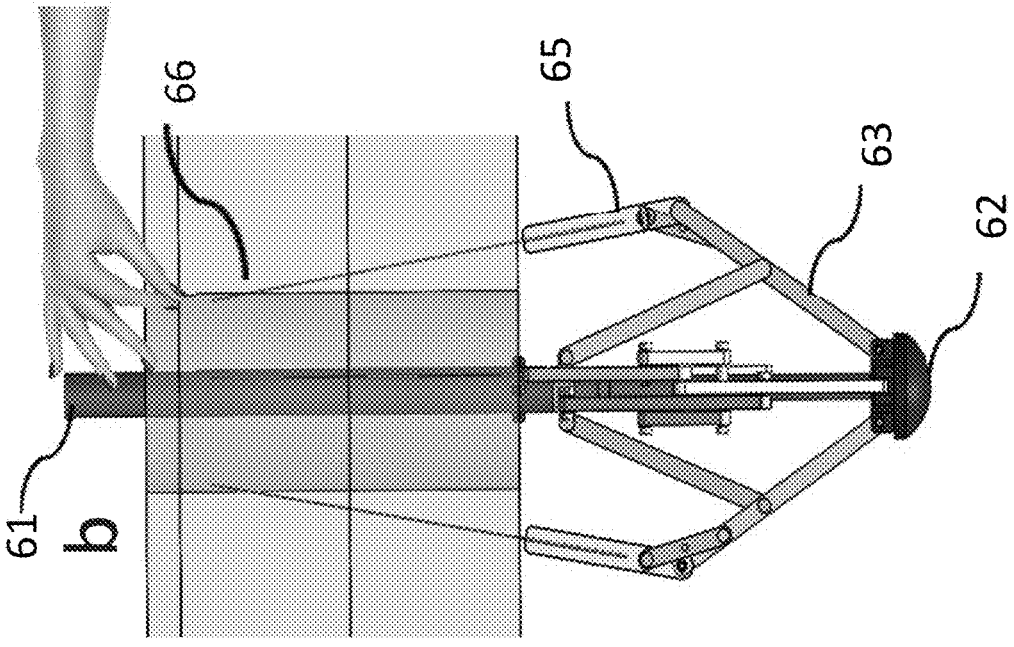
FIG. 6 schematically illustrates in an out of scale manner the operating of the (here e.g., 2 arms) umbrella configuration according to another embodiment of the invention.
Figure 6:
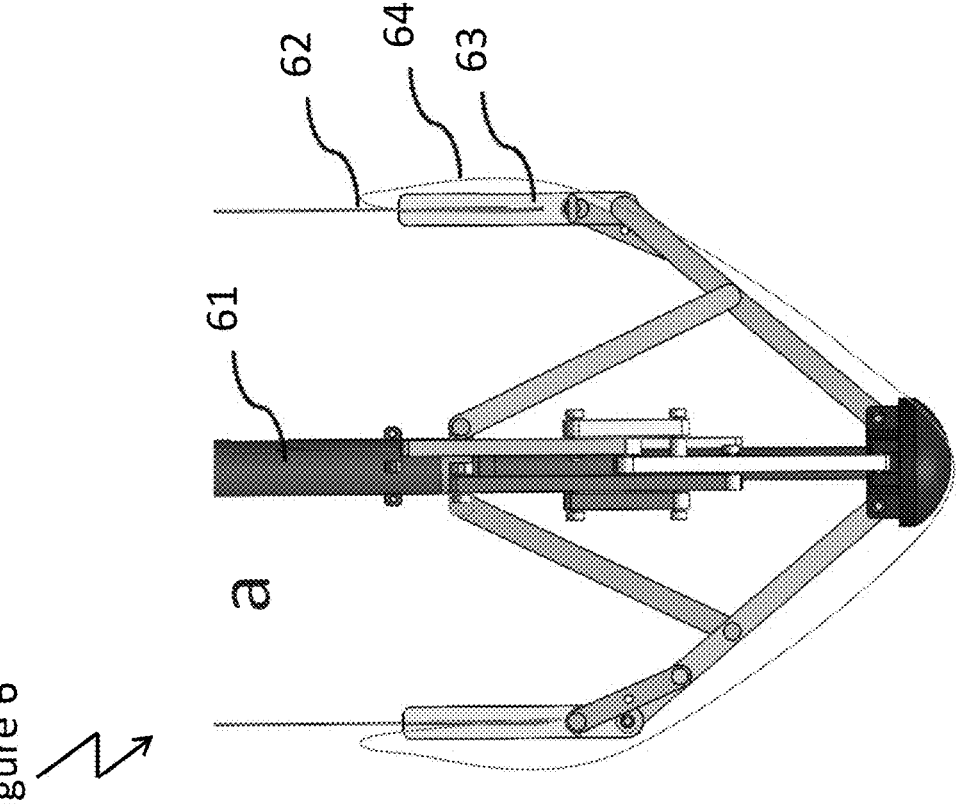

Reference is now made to FIG. 6, demonstrating the suturing of the opening. FIG. 6a shown the 'umbrella' configuration, in an open configuration. This presentation, the device is placed through the opening by the shaft 61. The needle 62 is held by the lower member 63 and connected to a suturing thread 64. FIG. 6b demonstrates the positioning of the needle, spanning the physiological layers, enabling the operator to grab the point and part of the body of the needle, so as to pull the suture through the opening, creating a suture.

Figure 7:
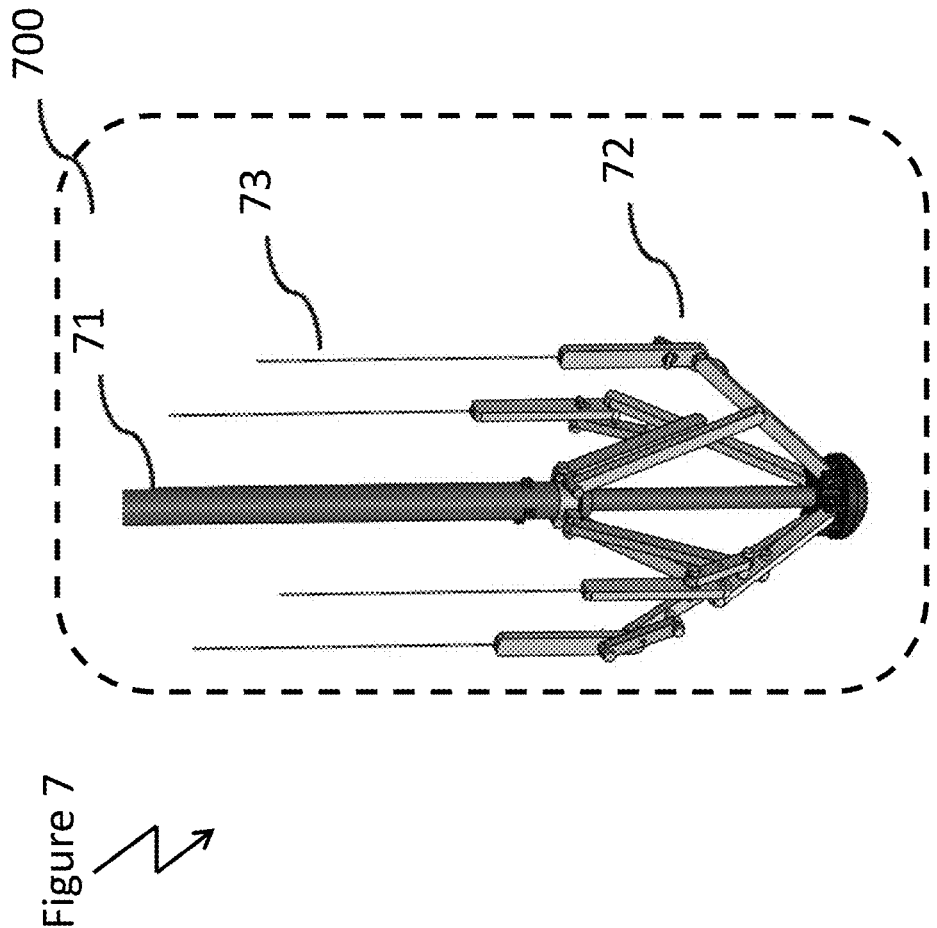
FIG. 7 schematically illustrates in an out of scale manner the (here e.g., 4 arms) umbrella configuration according to another embodiment of the invention.

Reference is now made to FIG. 7, presenting a second embodiment of the umbrella 700, the having a main stem connected to four ribs 72 and needles 73. The second configuration has the same mechanism as the two ribs configuration.

Figure 8:
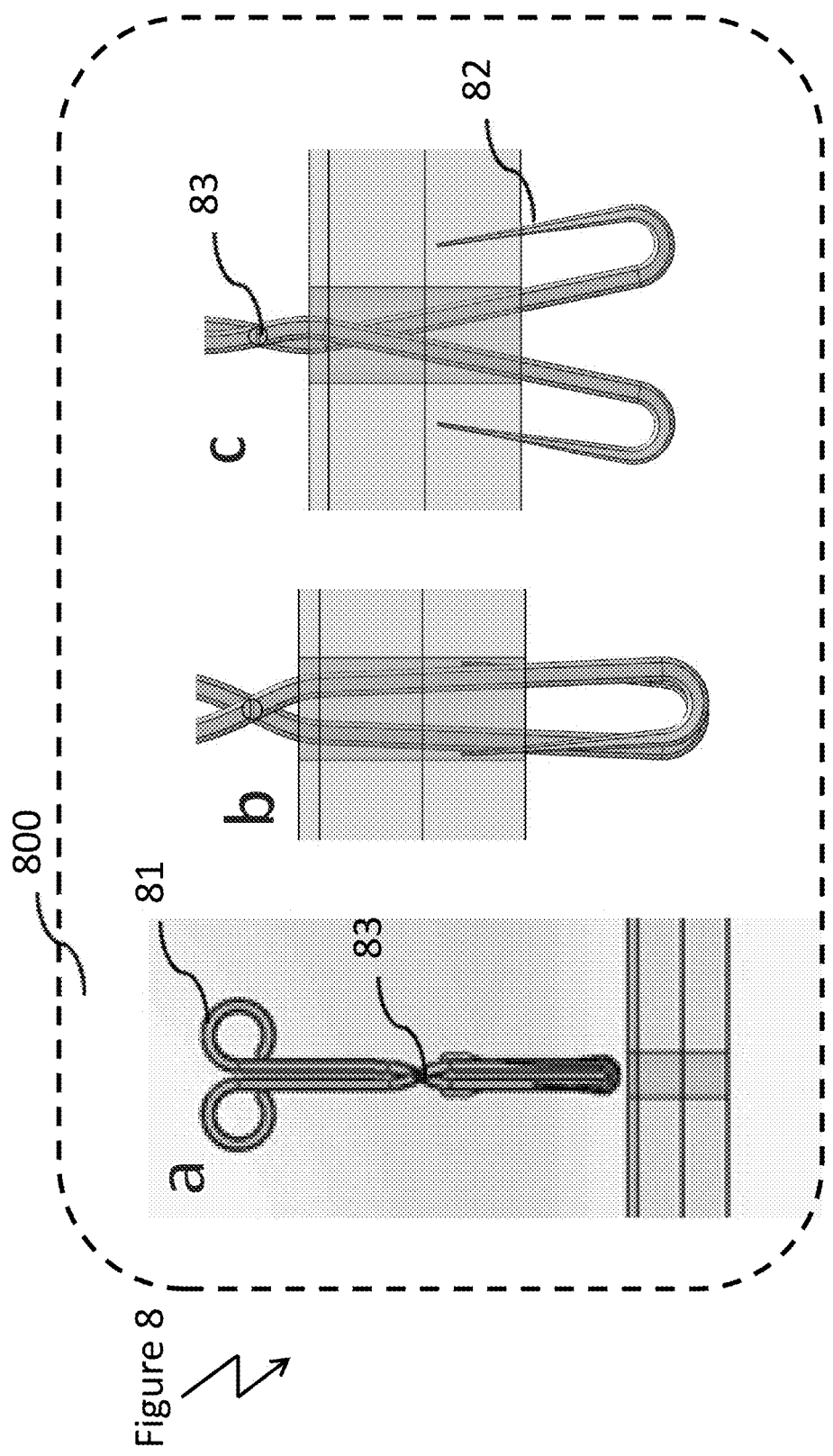
FIG. 8 schematically illustrates in an out of scale manner the 'scissor' configuration according to another embodiment of the invention.

An additional embodiment of the invention 800, herein referred to as the 'scissor' configuration, is constructed from two ribs, with the two ribs comprising a handle unit at the proximal end and a needle holding unit at the distal end. Reference is made to FIG. 8 showing the scissor configuration. The handle unit 81 is configured to enable positioning and handling of the device by an operator (such as a surgeon). The needle holding unit 82 is configured to hold the suture needle in a temporary and releasable manor. The two arms are linked by a hinge 83. FIG. 8 shows the operation of 'scissor' configuration; placing the device 8a, placing the device though the opening 8b and opening the device so as to position the needle outwards, towards the skin 8c.

Figure 9:
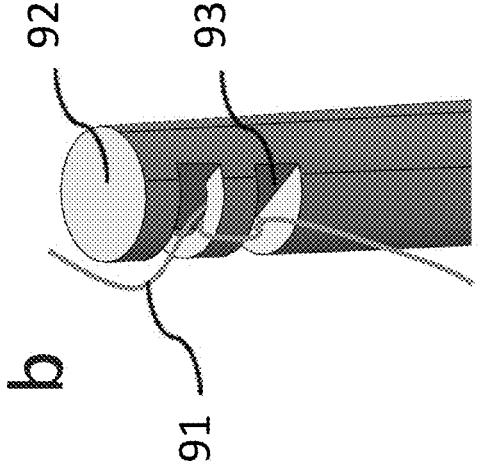
FIG. 9 schematically illustrates in an out of scale manner the thread holders of the scissor configuration according to another embodiment of the invention.
Figure 9:
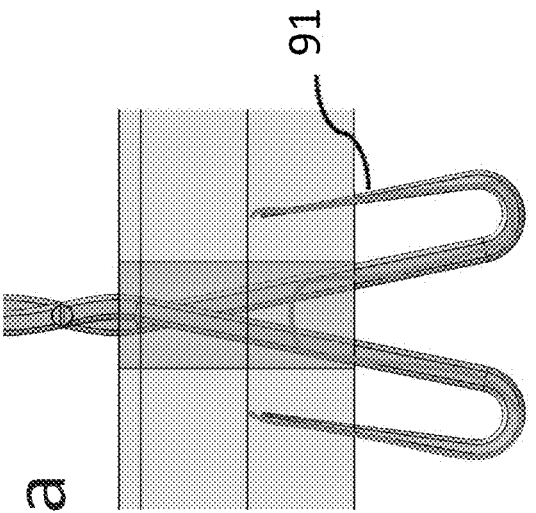
Figure 9:
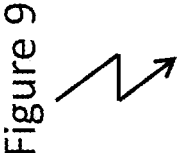

FIG. 9a show the device additional comprising a construct for holding and/or positioning a suture thread 91 by the distil end 92. The hold could be ridges, lips, flanges, rims, ribs, indents, pathways, hooks, brackets, shelfs, loops, hoops and rings. In some embodiment the construct has an opening 93 through which the thread 91 is held.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The description of the present invention has been presented for purposes of illustration and description, but is not intended to be exhaustive or limited to the invention in the form disclosed.

Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A device (300) for suturing and closing of laparoscopic incisions, comprising:
   a. a central stem (30, 43) having:
      i. An outer hollow shaft (31) with a distal end (31a) and a proximal end (31b); and
      ii. an inner shaft (32) with a distal end (32a) and a proximal end (32b) said inner shaft slidably accommodated within said outer hollow shaft (31);
   b. a plurality of ribs (34) each comprising
      i. an upper rib member (34a);
      ii. a lower rib member (34b) hingedly connected to said upper rib member by a locking joint (54), said lower rib member comprising a suture needle holder (36) at a free end; and
      iii. a middle rib member (53) connected to said upper rib member (34a) by a first hinge and connected to said lower rib member (34b) by a second hinge, said second hinge includes a locking mechanism (54) configured to secure, for each of said plurality of ribs (34), relative positions of said upper rib member (34a), middle rib member (53), lower rib member (34b) and hinges during use;
   c. a cap (33), mounted upon distal end of said inner shaft, said cap comprising a fifth hinge connected to said upper rib member (34a);

d. a plurality of rigid stretchers (35), each of said plurality of rigid stretchers (35) interconnected by a third hinge to the distal end of said outer shaft (31*a*) and by a fourth hinge to said upper rib member (34*a*);

said outer shaft configured to slide along the inner shaft and urge said rigid stretchers to extend from a closed configuration with rib, stretcher and shaft in substantially parallel contact, to an open configuration defined by an angle subtended between said inner shaft (32) and said rigid stretchers (35)

wherein said middle rib member (53) enables movement and pivoting of said suture needle holder (36), about a hinge axis connecting said middle rib member (53) and the lower rib member (34*b*).

2. The device of claim 1, wherein said ribs (34) are juxtaposed in pairs.

3. The device of claim 1, wherein the device, in its closed configuration, is capable of being inserted through a trocar or cannula, thereby ensuring a less invasive entry into a surgical area.

4. The device of claim 1, wherein said device is further configured to secure a suture thread, said thread following a path defined by said juxtaposed ribs (34) and said cap (33), said ribs (34) and said cap (33) comprising suture thread holds selected from ridges, lips, flanges, rims, ribs, indents, pathways, hooks, brackets, shelves, loops, hoops, eyes, eyelets and rings.

5. The device of claim 1, wherein said plurality of ribs (34*a*) have a locking joint (54), connecting said middle rib member (53) and said lower rib member (34*b*,52).

6. A method of suturing an opening in a patient, comprising steps of:

a. obtaining the suturing device of claim 1 and attaching at least one suture, each of said at least one suture comprising a suture needle and attached thread;

b. placing said device through a surgical opening into a surgical volume of the patient;

c. opening said device and locating a point of said suture needle around edges of said surgical opening;

d. bridging a body of said suture needle at least partially through physiological layers of said patient, a suture needle shaft within a grasp of a medical operator;

e. grasping said suture needle;

f. detaching said suture from said suturing device;

g. closing said suturing device;

h. removing said suturing device from said patent;

i. passing said at least one suture needle carrying said suture thread completely through said physiological layers of said patent; and j. stitching said opening.

7. The method of claim 6, additionally comprising a step of placing a trocar through said opening.

8. The method of claim 7, additionally comprising a step of removing said trocar through said opening.

* * * * *